(12) United States Patent
Koot et al.

(10) Patent No.: US 11,659,806 B2
(45) Date of Patent: May 30, 2023

(54) **TOBAMOVIRUS RESISTANT *SOLANACEAE* PLANT**

(71) Applicant: Dümmen Group B.V., De Lier (NL)

(72) Inventors: Johannes Theodorus Koot, De Lier (NL); Camillo Bérénos, De Lier (NL); Manuela Elizabeth Charlotte van Leeuwen-Uiterdijk, De Lier (NL); Paulus Cornelis Maris, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/979,911

(22) PCT Filed: Mar. 13, 2018

(86) PCT No.: PCT/EP2018/056282
§ 371 (c)(1),
(2) Date: Sep. 11, 2020

(87) PCT Pub. No.: WO2019/174721
PCT Pub. Date: Sep. 19, 2019

(65) Prior Publication Data
US 2021/0051910 A1  Feb. 25, 2021

(51) Int. Cl.
*A01H 6/82* (2018.01)
*C12Q 1/6895* (2018.01)
*A01H 5/02* (2018.01)

(52) U.S. Cl.
CPC .............. *A01H 6/82* (2018.05); *A01H 5/02* (2013.01); *A01H 6/821* (2018.05); *A01H 6/824* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

2018/0325057 A1  11/2018  Kosugi et al.

FOREIGN PATENT DOCUMENTS

| JP | 2014168429 A | 9/2014 |
| JP | 201786016 A | 5/2017 |
| JP | 2017212980 A | 12/2017 |
| WO | 2007097574 A1 | 8/2007 |

OTHER PUBLICATIONS

Cohen et al., "Susceptibility of Vegetatively Propagated Petunia to Tobamovirus Infection and Its Possible Control", HortScience, 1999, pp. 292-293, vol. 34:2.
Kim et al., "Delay of Disease Development in Transgenic Petunia Plants Expressing Cucumber Mosaic Virus I17N-Satellite RNA", J. Amer. Soc. Hort. Sci., 1995, pp. 353-359, vol. 120:2.
Nicoud et al., "Hypersensitive Reaction in Petunia: II. The Induction of Resistance and Soluble Leaf Proteins in TMV Infected Petunia Cultivars", J. Phytopathology, 1988, pp. 65-74, vol. 121.

*Primary Examiner* — Elizabeth F McElwain
(74) *Attorney, Agent, or Firm* — The Webb Law Firm

(57) ABSTRACT

Provided herein are plants belonging to the family of the Solanaceae such as plants of the genus *Petunia* and/or *Calibrachoa* and especially to Petunia plants which plants are resistant to the plant pathogen Tobamovirus amongst which the plant pathogens Tobacco mosaic virus, Tomato mosaic virus, Tobacco mild green mosaic virus and Pepper mild mottle virus. Further provided herein are methods for identifying Tobamovirus resistant plants of the Solanaceae family. Specifically, the present invention relates to plants belonging to the Solanaceae family, which plants are resistant to Tobamovirus and which plants comprise in its genome SEQ ID No. 1 and/or SEQ ID No. 3.

13 Claims, 4 Drawing Sheets

Specification includes a Sequence Listing.

FIGURE 2

2 week ELISA

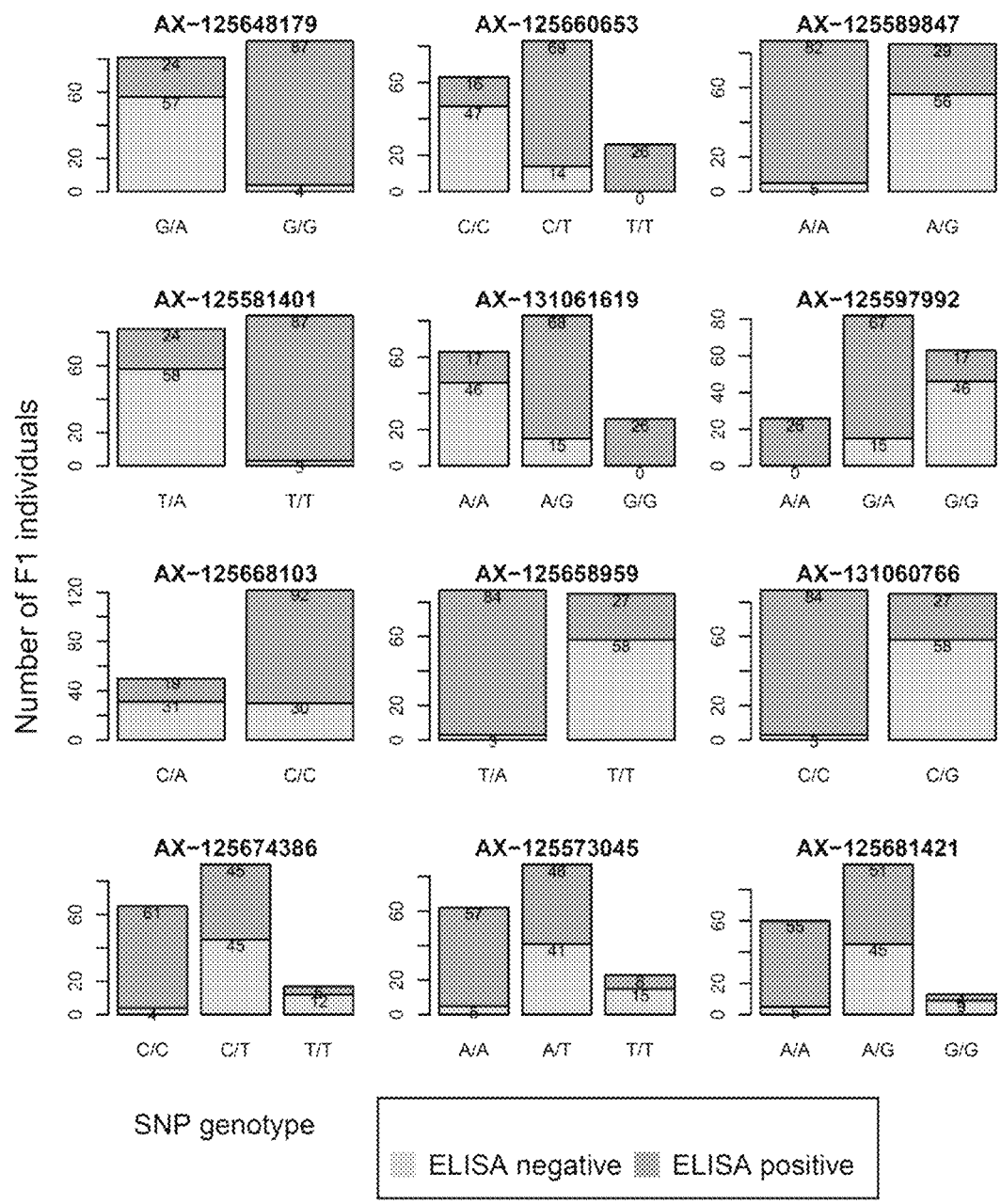

SEQUENCE LISTING

<160> NUMBER OF SEQ ID NOS: 10

<210> SEQ ID NO 1
<211> LENGTH: 23
<212> TYPE: DNA
<213> ORGANISM: Petunia

<400> SEQUENCE: 1
gccaaattgt ccaactactc agc                                             23

<210> SEQ ID NO 2
<211> LENGTH: 25
<212> TYPE: DNA
<213> ORGANISM: Petunia

<400> SEQUENCE: 2
aagccaaatt gtccaactac tcagt                                           25

<210> SEQ ID NO 3
<211> LENGTH: 25
<212> TYPE: DNA
<213> ORGANISM: Petunia

```
<400> SEQUENCE: 3
ctctgatcgt acctgtttct tcgtt                                          25

<210> SEQ ID NO 4
<211> LENGTH: 25
<212> TYPE: DNA
<213> ORGANISM: Petunia

<400> SEQUENCE: 4
ctctgatcgt acctgtttct tcgtc                                          25

<210> SEQ ID NO 5
<211> LENGTH: 24
<212> TYPE: DNA
<213> ORGANISM: Petunia

<400> SEQUENCE: 5
attccaataa cctcagcaac actg                                           24

<210> SEQ ID NO 6
<211> LENGTH: 30
<212> TYPE: DNA
<213> ORGANISM: Petunia

<400> SEQUENCE: 6
acctgtgaag ataaaartta agaatagcac                                     30

<210> SEQ ID NO 7
<211> LENGTH: 21
<212> TYPE: DNA
<213> ORGANISM: Artificial Sequence
<220> FEATURE:
<223> OTHER INFORMATION: L4tsp2r primer

<400> SEQUENCE: 7
ttccatactc aattggacat c                                              21

<210> SEQ ID NO 8
<211> LENGTH: 22
<212> TYPE: DNA
<213> ORGANISM: Artificial Sequence
<220> FEATURE:
<223> OTHER INFORMATION: L4std930F primer

<400> SEQUENCE: 8
gccactgtta acgtcacgac cc                                             22

<210> SEQ ID NO 9
<211> LENGTH: 20
<212> TYPE: DNA
<213> ORGANISM: Artificial Sequence
<220> FEATURE:
<223> OTHER INFORMATION: L2kstd975F primer

<400> SEQUENCE: 9
tcactcgtta ccactgagac                                                20

<210> SEQ ID NO 10
<211> LENGTH: 20
<212> TYPE: DNA
<213> ORGANISM: Artificial Sequence
<220> FEATURE:
<223> OTHER INFORMATION: L2kstd1629R primer
```

-continued

```
<400> SEQUENCE: 10
aacggatgga tgtccgattg                                              20
```

TOBAMOVIRUS RESISTANT *SOLANACEAE* PLANT

CROSS-REFERENCE TO RELATED APPLICATION

This application is the United States national phase of International Application No. PCT/EP2018/056282 filed Mar. 13, 2018, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2004839_ST25.txt. The size of the text file is 1,838 bytes, and the text file was created on Aug. 20, 2020.

DESCRIPTION

The present invention relates to plants belonging to the family of the Solanaceae such as plants of the genus *Petunia* and/or *Calibrachoa* and especially to Petunia plants which plants are resistant to the plant pathogen Tobamovirus amongst which the plant pathogens Tobacco mosaic virus, Tomato mosaic virus, Tobacco mild green mosaic virus and Pepper mild mottle virus. The present invention further relates to methods for identifying Tobamovirus resistant plants of the Solanaceae family.

The Tobacco mosaic virus (TMV), a plant pathogen species of the genus Tobamovirus, infects at least 199 different plant species from 30 families; however Solanaceous crops incur the most dramatic losses from the disease. Due to the easy spread of TMV, outbreaks can establish relatively quickly. Reductions in yield and quality attributed to Tobacco mosaic virus (TMV) infection of 60% loss in crop value were reported. TMV was estimated to cause a loss of one million US dollars each year between 1960 and 1965 in North Carolina's flue-cured tobacco. In 2000, TMV caused an estimated 1.4% loss in North Carolina's tobacco yield resulting in a 10.7 million US dollar loss.

TMV, Tomato mosaic virus (ToMV), Tobacco mild green mosaic virus (TMGMV) and Pepper mild mottle virus (PMMoV) are the most common viruses of the Tobamovirus genus which can infect Solanaceous crops. Tobamoviruses are transmitted through mechanical action and are able to survive on the seed surface or in the soil for periods of over a year and can stay infectious despite high temperature.

TMV is able to invade almost all tissues of a plant, except the root and shoot apices and the reproductive cells. Once infected, the plant cannot overcome the virus infection but the infection is usually not passed on to progeny seedlings through seed. Only a small percentage of progeny seedlings have been shown to inherit the viral infection through abrasion of young seedlings with the virus-contaminated seed coat during transplanting.

In tobacco cultivars lacking the N gene, TMV replicates and moves systemically, causing reduced plant growth and mosaic disease symptoms, characterized by intermingled areas of light and dark green leaf tissue. In contrast, TMV infection of N-containing tobacco produces cell death at the site of virus infection, and virus particles are restricted to the region immediately surrounding the necrotic lesions.

Tobamovirus infections have been reported in several species of the Solanaceae family, such as tobacco, pepper, tomato, eggplant, Datura, Physalis, Petunia and Calibrachoa. Spontaneous Tobamovirus resistance has been described in the literature for tobacco, pepper and tomato with one or more resistance gene identified as underlying such differences.

The mechanism of TMV resistance in plants is characterized by a hypersensitive response (HR) followed by a generic systemic acquired resistance (SAR) triggered by the interaction between the plant resistance gene and the virus avirulence gene. This mechanism of defense prevents virus dispersion by creating localized necrotic lesions around the infection site.

TMV infected tobacco plants were described for the first time in the middle of the $19^{th}$ century as carrying a contagious mosaic or leaf-spot disease. Not much was known about the disease agent at that time and it was named tobacco mosaic. Further research showed that this disease was caused by a virus and resulted in the identification of the TMV resistance gene N (for necrotic lesion response) in *Nicotiana glutinosa*. Currently, the N gene is the only and best characterized resistance gene to several tobamovirus strains. The N gene has a single dominant mode of action which involves encoding two transcripts (NS and NL) via alternative splicing. The NS transcript is predominant before and in the initial hours after TMV infection, while the NL transcript is predominant after 4 to 8 hours of infection. For complete resistance the balance between NS to NL transcripts before and after TMV infection is fundamental.

In tomato, symptomless plants despite the presence of TMV in their tissues were described. Subsequently several genes were identified that conferred resistance to TMV and Tomato mosaic virus (ToMV) in tomato. The first described resistance gene is $Tm_1$, soon followed by the discovery of $Tm_2$. A third gene, named $Tm-2^a$ or $Tm-2^2$ was discovered later. All three resistance genes have a dominant mode of action. $Tm-2^2$ is allelic to Tm-2 and differs in four amino acids. It is also the most durable and most widely used, as few ToMV isolates are able to break its resistance, and those that do, are generally less virulent.

In pepper, TMV resistance was first described in 1934 when screening 18 cultivars of *Capsicum annuum* and *Capsicum frutescens*. After TMV inoculation, Tabasco pepper plants showed necrotic local lesions followed by abscission of infected leafs (currently defined as a hypersensitive response), while other pepper cultivars showed secondary mottling during systemic infection. Further studies resulted in the identification of two TMV resistance genes in pepper; one dominant gene, named L for local lesion response, and a minor resistance gene named $l^i$. Currently, there are five L gene alleles (L1, L2, L3, L4 and L1a) characterized. Each was shown to provide resistance to different TMV pathotypes besides L1a which displays a different temperature sensitivity.

Furthermore, WO 2007/097574 discloses a molecular marker highly associated with TMV resistance in red pepper (*Capsicum chacoense*). By extrapolation, the application also discloses that this marker was predictive in other crops, such as cucumber, watermelon, red pepper, melon, Chinese cabbage, tobacco, Petunia, cotton and rose plants.

Resistance to Tobamoviruses conferred by resistance genes is typically not absolute. For example, in tomato, it is known that in general plants heterozygous for Tm2-2 are less resistant than homozygotes, that Tm2-2 mediated resistance is dosage-dependent and in both tomato (Tm-1 and Tm2-2 based) and tobacco (N-based) resistance is lower at higher temperatures. In heterozygotes, the incidence of systemic necrosis decreases with age at inoculation, increases with the duration of exposure to high temperatures, and decreases with the time interval of heat stress post inoculation. Different proxies for resistance can have different underlying genetics, despite a pleiotropic effect of the same gene. For example, in tomato, visual symptoms and inhibition of TMV replication are affected differently by Tm1 resistance genes, as symptoms are suppressed in a dominant fashion, whereas TMV multiplication is dosage-dependent.

In Petunia, infection by TMV occurs naturally and TMV outbreaks do occur and they have been known to impact 15% of the total US market and individual UK growers have experienced losses of up to 100k US dollars due to destruction of stock.

In vegetatively propagated crops, there is a high risk of virus transfer when cuttings are harvested. There are several ways to reduce the risk of TMV transmission in horticulture and floriculture. Besides basic hygienic measures, such as wearing disposable gloves, working in designated blocks and the prohibition of smoking in greenhouses, also chemical control is used. In tomato, disinfectants such as 2% Virkon and 10% Chlorox, but also Lysol all-purpose cleaner and nonfat dry milk (20%) were effective in preventing mechanical transmission of TMV. In Petunia, treatment of razor blades with similar agents was very effective in the prevention of transmission TMV. However, none of these measures can limit the spread completely, let alone prevent the occurrence of TMV, especially given the highly persistent nature of the virus particles.

TMV infected Petunia plants can display several symptoms, such as leaf mosaic, chlorotic molting, vein clearing, distortion of leaves and stems, reduced growth or stunting and even flower petal break. Five tobamovirus species have been shown to infect *Petunia hybrida* cultivars: TMV, ToMV, PMMoV, TMGMV and TSAMV (Tropical soda apple mosaic virus).

As of yet no known source of TMV resistance is known in commercial cultivars of *Petunia hybrida*. One study reported that some *Petunia hybrida* cultivars were able to remain symptomless after inoculation with TMV, but ELISA results showed that these plants were nevertheless infected. The characteristic hypersensitive response to TMV infection shown by tobacco, tomato and pepper plants carrying TMV resistance genes has also been reported for the Petunia species *Petunia axillaris* and *Petunia hybrida*. It was shown that one line of *Petunia axillaris* and 4 lines of *Petunia hybrida* displayed necrotic local lesions on inoculated leaves 7 days after inoculation (DAI) and 1 line of *Petunia axillaris* and 2 lines of *Petunia hybrida* plants did not show systemic infection 14 DAI. In the experiments disclosed, resistant lines were crossed with susceptible lines, and resulting in susceptible F1 offspring. This indicates a recessive mode of inheritance for the reported type of resistance. In another disclosure, plants of the *Petunia hybrida* cultivar "Bluepicoti" that were transformed by inserting Cucumber mosaic virus I17N-Satellite DNA showed delayed disease development upon infection with TMV.

SUMMARY

Considering the above, it is an object of the present invention, amongst other objects, to provide *Solanaceae* plants and especially Petunia and Calibrachoa plants which plants comprise a genetically encoded resistance to Tobamoviruses and especially resistance to TMV, ToMV, TMGMV and PMMoV.

The above object, amongst other objects, is met by the present invention as outlined in the appended claims.

Specifically, the above object, amongst other objects, is met by the present invention through providing plants belonging to the Solanaceae family, which plants are resistant to Tobamovirus and which plant comprises in their genome SEQ ID No. 1 and/or SEQ ID No. 3, preferably in homozygous form.

SEQ ID No. 1 comprises the nucleic acid C indicating a resistant plant while a susceptible plant comprises at the corresponding genomic position the nucleic acid T. Similarly, SEQ ID No. 3 comprises the nucleic acid T indicating a resistant plant while a susceptible plant comprises at the corresponding genomic position the nucleic acid C.

SEQ ID No. 1 and SEQ ID No. 3 are located on opposite sites of a Tobamovirus resistance providing gene, or genetic determinant, and accordingly, the present plants comprise both sequences in their genome. Further, because SEQ ID No. 1 and SEQ ID No. 3 flank the Tobamovirus resistance providing gene, or genetic determinant, the Tobamovirus resistance providing gene, or genetic determinant, can be readily isolated, for example from NCIMB 42982, and analyzed using generally available Molecular Biology techniques providing further means to introduce the present resistance gene into plants of the Solanaceae family, for example using transformation of plant cells and subsequently growing the transformed plant cells into mature plants. Also envisaged are modification techniques such as EMS mutagenesis or targeted mutagenesis to further modify the present resistance. Deposit NCIMB 42982 was deposited on Mar. 6, 2018 at National Collections of Industrial, Food and Marine Bacteria (NCIMB), NCIMB Limited, Ferguson Building; Craibstone Estate, Bucksburn Aberdeen, Scotland, AB21 9YA United Kingdom.

According to a preferred embodiment, the present plants are members of the Solanaceae subfamily of the Petunioideae.

According to another preferred embodiment, the present plants are species within the genera *Petunia, Calibrachoa* or *Petchoa. Calibrachoa* are evergreen short-lived perennials and subshrubs with a sprawling habit, with small petunia-type flowers. Although *Calibrachoa* are closely related to *Petunia*, it has been found that there are important differences in chromosomes, corresponding to external differences and fertilization factors that distinguished the two genera. It is noted that *Petchoa* is a hybrid genus derived from crossing *Calibrachoa* and *Petunia*.

According to yet another preferred embodiment, the present plants are species within the genus *Petunia* selected from the group consisting of *Petunia alpicola, Petunia axillaris, Petunia bajeensis, Petunia bonjardinensis, Petunia exserta, Petunia guarapuavensis, Petunia inflata, Petunia integrifolia, Petunia interior, Petunia ledifolia, Petunia littoralis, Petunia mantiqueirensis, Petunia occidentalis, Petunia patagonica, Petunia reitzii, Petunia riograndensis, Petunia saxicola, Petunia scheideana, Petunia villadiana, Petunia violaceae* and hybrids thereof such as, preferably, *Petunia hybrida*.

According to an especially preferred embodiment, the present resistance is a semi-dominant Tobamovirus resistance identical to the resistance gene, between SEQ ID No. 1 and SEQ ID No. 3 as found in deposit NCIMB 42982. The deposit comprises seed obtained after selfing a plant from population 2 (see below) being heterozygous for SEQ ID No. 1 and SEQ ID No. 3. The deposit contains homozygous resistant, heterozygous resistant and homozygous susceptible seeds in a predicted Mendelian ratio of 1:2:1, respectively.

According to another especially preferred embodiment, the present resistance is a semi-dominant Tobamovirus resistance derived, from deposit NCIMB 42982 or the present resistance is the resistance of deposit NCIMB 42982.

The present Tobamovirus resistance is preferably selected from the group consisting of TMV resistance, ToMV, TMGMV resistance and PMMoV resistance, more preferably Tobacco mosaic virus resistance.

The present plants preferably do not comprise in their genome SEQ ID No. 2 and/or SEQ ID No. 4. Formulated differently, the even numbered SEQ ID Nos. represent genomic sequences associated with the susceptible gene.

According to a most preferred embodiment of the invention, the present plants are Petunia plants resistant to TMV due to the presence of SEQ ID No. 1 and/or SEQ ID No. 3 in their genome, preferably due to the presence of SEQ ID No. 1 and SEQ ID No. 3 in their genome.

Considering the above, the present invention relates to, according to another aspect, methods for identifying a Tobamovirus resistant plant, the methods comprise the step of establishing the presence of SEQ ID No. 1 and/or SEQ ID No. 3, preferably in homozygous form, in the genome of said plant.

According to a preferred embodiment, the present methods comprise the further step of establishing the absence in the genome of SEQ ID No. 2 and/or SEQ ID No. 4.

According to yet another preferred embodiment, the present method establishing the presence or absence of the respective SEQ ID Nos. comprises nucleic amplification and subsequent analysis of the amplification products. Nucleic acid amplification and analysis techniques are readily available and known to the skilled person.

The plants to be identified using the present methods are preferably Tobamovirus resistant Petunia plants selected from the group consisting of *Petunia alpicola*, *Petunia axillaris*, *Petunia bajeensis*, *Petunia bonjardinensis*, *Petunia exserta*, *Petunia guarapuavensis*, *Petunia inflata*, *Petunia integrifolia*, *Petunia interior*, *Petunia ledifolia*, *Petunia littoralis*, *Petunia mantiqueirensis*, *Petunia occidentalis*, *Petunia patagonica*, *Petunia reitzii*, *Petunia riograndensis*, *Petunia saxicola*, *Petunia scheideana*, *Petunia villadiana*, *Petunia violaceae* and hybrids thereof, preferably *Petunia hybrida*.

Resistance phenotype to be identified using the present methods is preferably a phenotype providing resistance to one or more viruses of the group consisting of Tobacco mosaic virus resistance, Tomato mosaic virus resistance, Tobacco mild green mosaic virus resistance and Pepper mild mottle virus resistance.

BRIEF DESCRIPTION OF THE DRAWINGS

The present invention will be further detailed in the following example. In the example, reference is made to figures wherein:

FIG. 2: shows the proportion of plants with ELISA positive results 2 weeks after inoculation (2WAI) in bio-assay 2 as function of temperature for the TMV-A isolate and TMV-U isolate separately. F1 genotypes were grouped based timing of TMV detection by ELISA in bio-assay 1;

FIGS. 3A-3B: show graphs showing the number of ELISA negative and ELISA positive plants for each of the 20 most significantly associated SNP on the SNP chip with a unique segregation pattern in population 1. Results are ordered from left to right and top to bottom based on a decreasing order of the strength of their association in the marker-trait analysis.

DETAILED DESCRIPTION

EXAMPLE

Introduction

Figure 1:
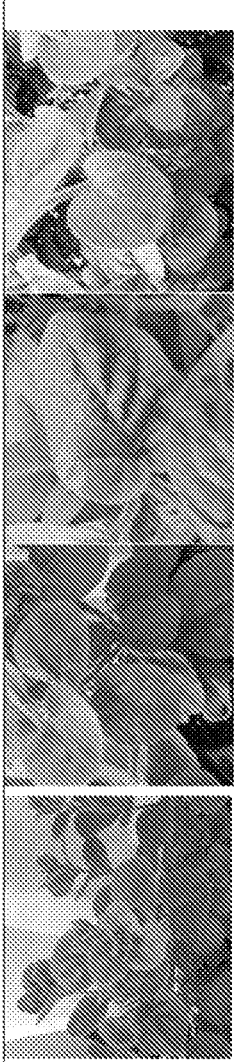
FIG. 1: shows symptoms of TMV infection. −) no lesions on inoculated leaf; +) small local lesions on inoculated leaf; ++) big local lesions, partly black vein; +++) heavy local lesions, veins infected and necrotic leaf; systemic head symptoms showing necrotic spots in top leaf, mosaic pattern; curling of the top leaves.

The present example discloses the number, effect sizes and genetic positions of quantitative trait loci (QTLs) underlying TMV resistance in a segregating diploid F1 population of *Petunia hybrida*. Disclosed is a major effect QTL on one linkage group, indicative of a monogenic inheritance. The association with resistance was strong, as 70% of all individuals of one genotype were tested negative for systemic TMV infection using ELISA 2 weeks after inoculation (2WAI) and 98% of individuals carrying the other susceptible genotype were tested positive for TMV infection 2 WAI. The quantitative resistance is temperature dependent, such that resistance is higher when plants are maintained at lower temperatures (21° C.) than at higher temperatures (31° C.).

Methods

Population Development

Two cuttings of accession TT-0115 were tested for TMV resistance using mechanical inoculation. One cutting did show clear symptoms and was tested positive 5 weeks after inoculation. The other cutting was symptomless 7 weeks after inoculation. A mother plant was established and coded TT15-001414-001. Four cuttings from this mother plant were again inoculated and remained symptomless for 5 weeks, confirmed with negative ELISA results.

New cuttings from the mother plant were used as parent for crosses with two susceptible varieties: TT07-005643-044 and TT08-003356-033.

Bio-Assays

Bio-Assay 1: Screening of the Mapping Populations

Fresh cuttings taken from mother stock plants derived from F1-plants derived from above mentioned crosses were stuck in coconut peat plugs and grown for two weeks for root establishment. Five cuttings were stuck, of which four were inoculated and one was used as negative control. Cuttings were rooted in 28-well trays for 2 weeks, with one label for each four plants for the inoculated material. Control plants were labelled individually. One week after transplanting to 10 cm pots, plants were inoculated with TMV-A. *Nicotiana rustica*, an experimental host for TMV, was used as control plant to confirm infectiousness of the TMV inoculum used. Greenhouse conditions were 20° C./18° C. D/N with day length of 14 hours. F1-population size was 208 and 295 for ♀ TT15-001414-001×♂ TT07-005643-044 (as well as the reciprocal cross, hereafter referred to as Population 1) and TT15-001414-001×TT08-003356-033 (as well as the reciprocal cross, hereafter referred to as Population 2), respectively. Seven susceptible genotypes (including both susceptible parents), resistant parent and resistant grand-parent were used as references.

The original source of TMV was an infected Petunia 1820 found in 2012 in a greenhouse in the Netherlands. The virus was maintained in-house on susceptible Petunia 1820. The isolate was named TMV-A. Leaves from infected inoculum plants were collected and ground together with inoculation buffer (NaH$_2$PO$_4$) Filtered inoculum was kept on ice during inoculation.

Prior to inoculation, carborundum powder was dusted onto the leaves of the plants. Plants were inoculated by dipping a finger (with gloves) into inoculum and rubbing two fully expanded leaves 5-7 times each. After each leaf, finger was dipped again in the inoculum.

Two weeks after inoculation (WAI), plants were phenotypically scored, using two visual scoring scales. The inoculated leaves were scored based on their local lesions in four different classes and top part of the plant was scored based on presence of systemic head symptoms and curling of top leaves (FIG. 1). After visual screening, plants were sampled for serological tests using ELISA. For this test, 4 plants of each genotype were bulked and tested as one sample. There were four possible outcomes of a serological ELISA test based on the $OD_{405NM}$-values, which were corrected for the negative controls (Table 1).

TABLE 1

Overview of the how ELISA scores are classified based on $OD_{405NM}$-values corrected for blanked data.

| | |
|---|---|
| Negative | <0.100 |
| Inconclusive | 0.101-0.200 |
| Positive | >0.200 |
| No result | No result |

Four (Pop 2) and five weeks (Pop 1) after inoculation, plants were scored again for head symptoms and sampled for ELISA testing. For each genotype that was tested negative by ELISA, one plant was kept for a prolonged assay which was maintained until 27 weeks after sticking or discarded earlier when tested positive by ELISA. All resistant and susceptible references that were included in the bio-assay were also kept if plants were still sufficiently viable. Plants were trimmed and potted in 13 cm pots. Nine (Pop 2) and ten weeks (Pop 1) after inoculation, individual plants were scored again for head symptoms and positive plants were discarded. Symptomless plants were inoculated again, using the same method as the initial inoculation method.

The plants were scored for local lesions on inoculated leaves and on head symptoms 2 weeks after re-inoculation. Plants were tested for the presence of viral antigen using ELISA 2 times, namely 17 WAI and 22 WAI.

Bio-Assay 2: Determining the Effect of Temperature on TMV Resistance

After initial phenotyping, a trial was performed to assess temperature-dependency of resistance. Genotypes from 4 different groups of pop 2 were used: 1) Positive ELISA 2 WAI; 2) positive ELISA 17 WAI; and 3) ELISA negative throughout the experiment (N=15, 3, 16 and 9 genotypes respectively). The resistant grandparent (TT-0115), the resistant parent (TT15-001414-001) and the susceptible parent (TT08-003356-033) were included as controls. Two day/night temperature regimes were applied: 21° C./19° C. and 31° C./25° C. Two TMV isolates were used, the original Petunia isolate (TMV-A) and one isolated from tomato (TMV-WU). For each temperature/TMV isolate combination, two plants per genotype were inoculated. In each temperature regime, there was a mock-inoculated control plant for each genotype. Each plant was individually labeled, scored and sampled.

Plants were scored with same scoring scale mentioned above (FIG. 1) and were sampled two and four weeks after inoculation on an individual basis.

2 WAI ELISA was performed and data coded as 1 for ELISA negative and 0 for ELISA positive was analyzed in a mixed model using the glmmPQL function in the R package MASS. Fixed effects included in the model were temperature, resistance grouping in bio-assay 1 and virus isolate. Pedigree Item was fitted as a random effect to take into account the repeated measures for each genotype and a binomial error structure was used.

Prior Art Screening

SEQ ID Nos disclosed in WO 2007/097574 and a panel consisting of the resistant source and 3 Petunia genotypes that were tested ELISA positive for TMV and/or ToMV were tested. Two PCR reactions were performed for two separate primer pairs. The first reaction was run using disclosed Seq ID 6 and Seq ID 8, and the second was run using disclosed Seq ID 9 and Seq ID 10. Red pepper was used as a positive control. If resistance in the present plants would correspond with the disclosure of WO 2007/097574 fragment length of the amplicons would differ between the resistant and susceptible Petunia accessions.

Linkage Mapping

All F1 plants and their parents were genotyped using a custom-made 45K Affymetrix SNP array containing 45,000 single nucleotide polymorphisms (SNP). For each parent, two replicates were genotyped. Quality control was performed as follows. First, only SNPs with Affy calls PHR_notPassingPSgenotypes and notPHR_notPassingPSgenotypes were retained. Then, using the check.marker function in GenABEL, loci with call rate <90%, SNPs that segregated 100% identically with another SNP and individuals with call rate <95% were removed. Individuals showing identical-by-state >99% were also removed. The resulting dataset consisted of 1,565 SNP and 920 markers for population 1 and population 2 respectively.

Subsequently, a linkage map was constructed using the R package onemap for population 1 only. Only SNP markers that segregated AB×AA (source heterozygous, susceptible parent homozygous) or segregated AB×AB (both parents heterozygous) were used and prior to linkage mapping SNPs that showed Mendelian errors or severe segregation distortion (P<0.000000005) were also excluded.

SNP markers were assigned to linkage groups using the group function, with LOD scores of 30 and maximum recombination frequencies of 0.4. Within linkage groups, SNP markers were ordered with the record function (LOD=10, max. rf=0.4) and the Kosambi mapping function was used. Subsequently, SNP markers that were excluded prior to linkage mapping due to their co-segregation with other SNPs were given the same linkage groups and positions.

Association Mapping

2 WAI ELISA results were used as a proxy for TMV resistance and were modelled using a binomial error distribution in both populations independently. Plants with inconclusive ELISA results were omitted from the analysis. First, the proportion of phenotypic variance explained by all SNP markers that passed quality control (QC) was analyzed using the polygenic function in GenABEL with weight set to "no". Second, residuals from this model were analyzed using the qtscore function.

Marker Validation, Fine Mapping and Germplasm Screen

For unique contigs spanning the QTL region, SNPs were mined that were heterozygous in the source and homozygous in all other accessions for which genome or transcriptome sequence data was available. KASP assays were designed for 24 SNP markers which were found on 17 contigs (shown in Table 2). These were run on the parents and 84 F1 plants to confirm the parental genotypes and expected segregation pattern. SNPs that did fulfill these criteria were then run on a total of 464 individuals, 195 individuals from pop 1 and 269 individuals from pop 2. The strength of the association was tested with ELISA results using Chi-square tests. 145 diverse accessions were screened representing the genetic diversity present in Petunia cultivars using the 7 most significantly associated SNPs using KASP assays.

TABLE 2

Primers used for KASP assays of SNPs significantly associated with TMV resistance in the *Petunia* F1 population. The haplotype targeted by each forward primer is shown, as well as the flanking sequence surrounding the SNP. The haplotype marked in bold targets the resistant haplotype.

| Contig No. and Primer set Nr | Contig/SNP | Primer | Targeted haplotype | Primer sequence |
|---|---|---|---|---|
| Set 1 | >PET_T310214\|C62940_5790 | 18-0001 - Rev1 | T | AAGCCAAATTGTCCAACTACTCAGT (SEQ ID No. 2) |
| | | 18-0002 - Rev2 | C | GCCAAATTGTCCAACTACTCAGC (SEQ ID No. 1) |
| | | 18-0003 - Fw | | ATTCCAATAACCTCAGCAACACTG (SEQ ID NO: 5) |
| Set 2 | >PET_T36154\|C53573_29679 | 18-0004 - Fw1 | C | CTCTGATCGTACCTGTTTCTTCGTC (SEQ ID No. 4) |
| | | 18-0005 - Fw2 | T | CTCTGATCGTACCTGTTTCTTCGTT (SEQ ID No. 3) |
| | | 18-0006 - Rev | | ACCTGTGAAGATAAAARTTAAGAAT AGCAC (SEQ ID No. 6) |

RESULTS

Results Bio-Assay 1

Phenotyping was done two weeks after first inoculation (2 WAI), with sampling for ELISA in the same week. ELISA results for 2 WAI are presented in Table 3. Plants that were tested negative and inconclusive were re-inoculated and further ELISA tests were done. For population 1 this resulted in 65 plants and for population 2 there were 83 plants tested using ELISA 13 WAI of which 53 and 74 tested ELISA negative, respectively (Table 4).

All plants tested negative and inconclusive at 13 WAI were tested again four weeks later (17 WAI). In pop one 19 out of 57 did test negative and 37 out of 77 did test negative in pop 2 (Table 5). The last ELISA test was 22 WAI. For population one 12 plants were still tested ELISA negative and for population two 18 plants remained negative (Table 6)

TABLE 3

ELISA results of plants sampled two weeks after inoculation (2 WAI). Four plants of each genotype were bulked and tested as one sample.

| | | | | | |
|---|---|---|---|---|---|
| Population 1 | 208 | 115 | 69 | 17 | 7 |
| Population 2 | 295 | 176 | 78 | 18 | 23 |

*$OD_{405NM}$ > 0.2 during the ELISA
**$OD_{405NM}$ < 0.1 during the ELISA
***Inconclusive: $OD_{405NM}$ between 0.101 and 0.2 during the ELISA
****Plants were too small to inoculate and/or sampled for ELISA testing

TABLE 4

ELISA results of plants sampled 13 WAI.

| | | | | |
|---|---|---|---|---|
| Population 1 | 65 | 10 | 53 | 2 |
| Population 2 | 83 | 8 | 74 | 1 |

TABLE 5

ELISA results of plants sampled 17 WAI. Plants have been repotted 10 WAI and re-inoculated 14 WAI.

| | | | | |
|---|---|---|---|---|
| Population 1 | 57 | 34 | 19 | 4 |
| Population 2 | 75 | 36 | 37 | 2 |

TABLE 6

ELISA results of plants sampled 22 WAI. Plants have been repotted 10 WAI and re-inoculated 14 WAI.

| | | | | |
|---|---|---|---|---|
| Population 1 | 22 | 10 | 12 | |
| Population 2 | 39 | 19 | 18 | 2 |

Results Bio-Assay 2

Figure 2:
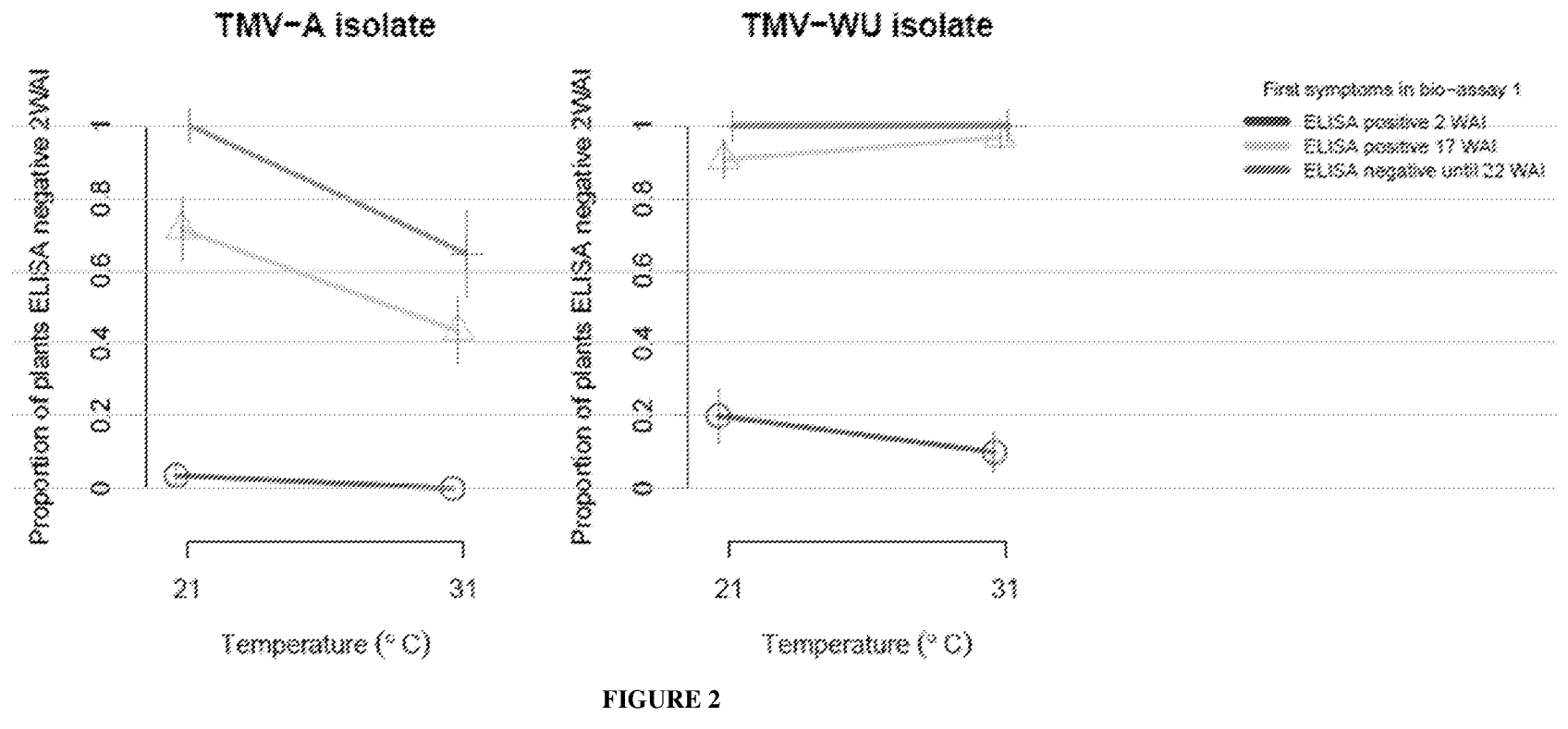

Two weeks after inoculation no difference was observed between 21° C. and 31° C. ELISA results in the susceptible group tested with the TMV-A isolate (Table 7). Almost all of the genotypes that scored positive for the ELISA 2WAI in bio-assay 1, did score positive two weeks after inoculation in bio-assay 2 and no difference between the temperature treatments or isolates was observed. However, in the groups that showed first ELISA positive results 17WAI or showed no ELISA positive results throughout the experiment of bio-assay 1, the proportion of individuals with ELISA positive results was higher at higher temperatures, indicating that resistance did not hold up in time at higher temperatures. Overall, resistance was significantly lower at 31° C. than at 21° C. (Table 7, Table 8, and FIG. 2).

There was also a significant difference in plant response to TMV-A isolate (used in population screening) and TMV-WU isolate. The TMV-A isolate, which was used to inoculate the populations used for QTL mapping, showed to be able to infect more plants at both temperatures (Tables 7 and 8). Overall, using the TMV-A isolate, the proportion of F1 individuals with a single copy of the resistance allele with ELISA negative results 2WAI decreased from 75% at 21° C. to 62% at 31° C. Using the TMV-WU isolate, a substantially smaller decrease in resistance was observed in the heterozygous F1 plants (21° C.: 93% ELISA negative 2WAI; 31° C.: 92% ELISA negative 2WAI), though the interaction between temperature and isolate was not significant (results not shown).

TABLE 7

ELISA results on individual plants for the heat dependent resistance experiment, sampled 2 weeks after inoculation (2 WAI). Summary statistics of the proportion of plants with ELISA negative results for low (21° C.) and high temperatures (31° C.) are presented for the TMV-A and TMV-WU isolates separately.

| Grouping based on Bio-assay 1 | Genotypes | Sample size | 21° C. Proportion ELISA negative 2 WAI | 31° C. Proportion ELISA negative 2 WAI | 21° C. Proportion ELISA negative 2 WAI | 31° C. Proportion ELISA negative 2 WAI |
|---|---|---|---|---|---|---|
| ELISA positive 2 WAI | 15 | 30 | 0.03 | 0 | 0.2 | 0 |
| ELISA positive 17 WAI | 16 | 32 | 0.63 | 0.41 | 0.91 | 0.94 |
| ELISA negative throughout the exp | 9 | 18 | 0.94 | 0.61 | 0.89 | 1 |

TABLE 8

Parameter estimates of a mixed model analyzing 2WAI ELISA results as a function of temperature, virus isolate and ELISA results in bio-assay 1. Water controls were excluded from this analysis. The model shows that expression of resistance is negatively affected by temperature and that it can be influenced by the virus isolated used as well. Positive parameter estimates indicate an increased level of resistance (2WAI negative results using ELISA).

| | Parameter Estimate | Standard Error | Degrees of Freedom | T-value | P |
|---|---|---|---|---|---|
| (Intercept) | −1.87 | 1.03 | 262 | −1.82 | 0.070 |
| Temperature | −0.13 | 0.03 | 262 | −3.68 | <0.0001 |
| Isolate TMV-WU | 2.96 | 0.46 | 262 | 6.49 | <0.0001 |
| ELISA positive 17 WAI | 5.57 | 0.76 | 37 | 7.37 | <0.0001 |
| ELISA negative | 7.25 | 0.93 | 37 | 7.78 | <0.0001 |

Confirmation that the Source of Resistance is not Disclosed in WO 2007/097574

For the PCR using primers Seq ID 6 and Seq ID 8, no difference in fragment length was observed between the resistant accession and the susceptible accessions. A PCR with primers Seq ID 9 and Seq ID 10 yielded no amplification in any of the Petunia samples. Fragments were observed for both primer pairs in red pepper. This unequivocally establishes that the present source of resistance is not disclosed in WO 2007/097574.

Linkage Mapping

A total of 1,064 uniquely segregating SNP were assigned to 16 linkage groups. Adding co-segregating SNPs to the map resulted in a linkage of 5635 segregating SNPs. Adding SNPs that were present on the SNP chip but omitted after QC resulted in a total of 10973xSNPs on 4572 unique contigs. A total of 8 LGs contained more than 200 SNPs, and the remaining linkage groups contained less than 40 SNPs.

Association Mapping

ELISA results (viral antigen presence) were highly heritable in population 1, as 90% of phenotypic variance was explained by SNPs. Genomic heritability was slightly lower in population 2 as 67% of phenotypic variance was explained by genotyped SNPs which can be explained by the substantially lower amount of SNPs passing quality control. The most significantly associated SNPs were all found on LG 6, and the distribution of P values showed a steep unimodal shape indicating that there is likely a single QTL affecting TMV resistance.

The contig containing the SNP that showed the strongest association was shared between population 1 and 2, corroborating the results obtained in population 1 alone.

Figure 3A:
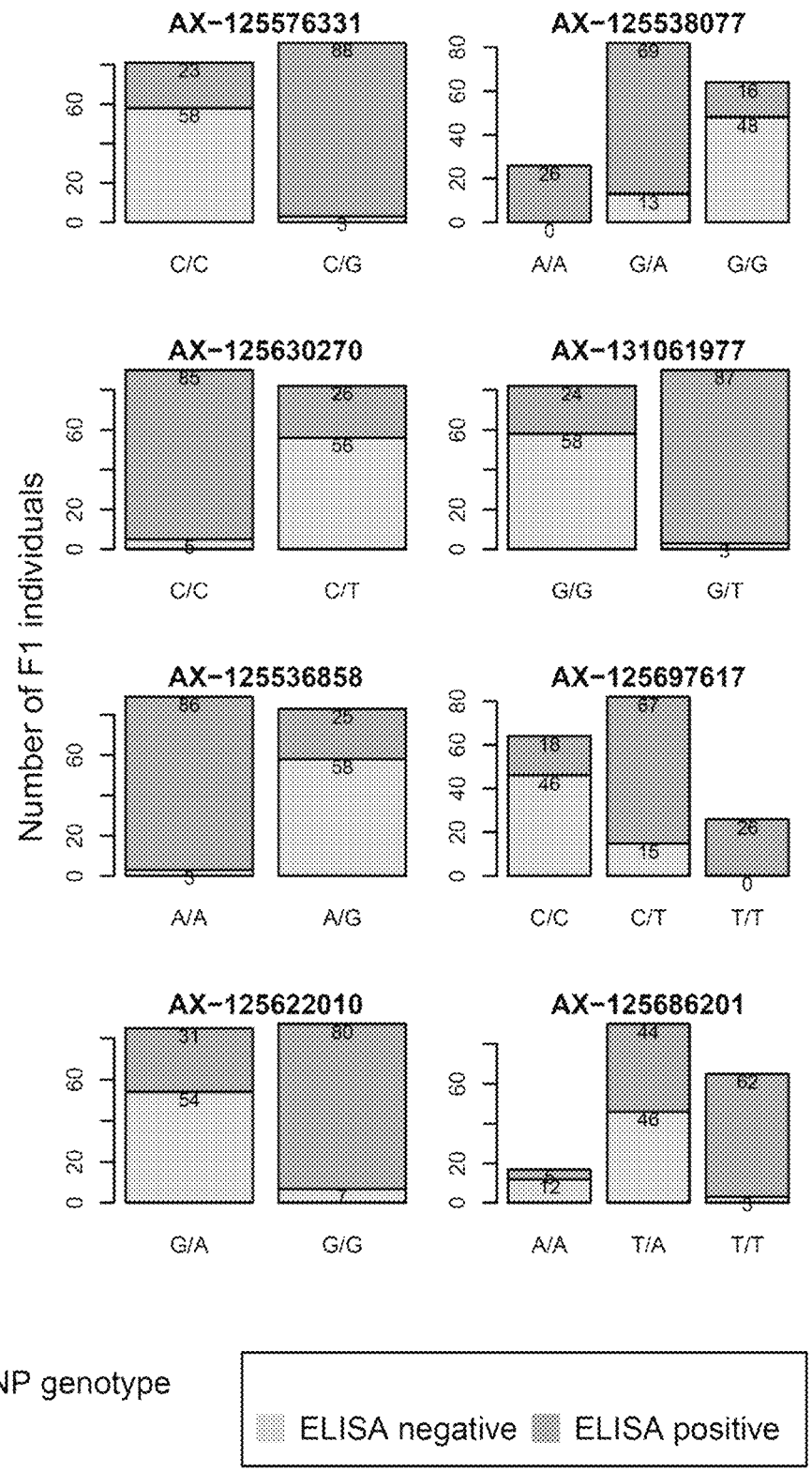

The most significant SNP (positioned at 80.3 cM on LG 6) exhibited 2 genotype classes in population 1 and 71.6% of individuals with one genotype were ELISA negative, while 96.7% of individuals with the other genotype were ELISA positive. The predictive power of other SNPS was weaker, as expected based on their lower P values (FIG. 3).

Validation with KASP Assays and Fine-Mapping

For 19 out of the 24 KASP assays that were designed clearly separated clusters were observed and could genotypes be called confidently. In total 464 F1 plants (of which 430 with clear TMV ELISA data and 34 with inconclusive ELISA results) were genotyped at these 19 SNPs using KASP assays: 195 individuals from population 1 and 269 individuals from population 2. 36 F2 plants were also tested to screen for individuals carrying homozygous resistant haplotypes. Three individuals with homozygous resistant haplotypes were found, which were used as additional samples to improve genotype calling. The parents from both populations were used as control samples as well as TT-0115, the resistant grandparent of the F1 populations. In all KASP assays, the resistant parent and grandparent (TT15-001414-001 and TT-0115 respectively) scored heterozygous and the susceptible parents (TT07-005643-044 and TT08-00356-033) homozygous for the susceptible haplotype.

Call rate varied between KASP assays, but for each SNP between 406 up to 423 F1 plants with 2WAI ELISA data were successfully genotyped. When looking at the association between KASP genotypes and 2WAI ELISA results (viral antigen presence) an accuracy was found for predictive resistant genotypes between 58 and 66% and for susceptible genotypes between 95 and 98% (Table 9).

Overall, PET_T36154|C53573_29679 (at 79.584 cM) has the highest predictive power when predicting resistance across both F1 populations (65.8% of plants with the resistant genotype were ELISA negative), as well as when it comes to susceptibility (97.5% of F1 plants with susceptible genotype were ELISA positive, results shown in Table 9). This SNP was also most strongly associated with 2WAI ELISA results (logistic regression, $P=1*10^{-42}$) closely followed by PET_T310214|C62940_5790 at 75.931 cM ($P=2.84*10^{-42}$). Other SNPs were substantially less significantly associated, confirming the linkage map positions, and indicating that these two SNPs are likely flanking the causal gene (Table 9). The distance between PET_T36154|C53573_29679 and PET_T310214|C62940_5790 is only 3.6 cM using the linkage map genetic distance which means that either marker is in closer proximity than 1.8 cM from the causal gene

TABLE 9

Results for the association between 2 WAI ELISA (presence of viral antigen) and individual SNPs in the QTL region using KASP assays. Genotype data from both population 1 and 2 were combined for the analyses. P values were obtained by fitting a logistic regression with ELISA results 2 WAI as a binary response variable and SNP genotype as a dependent variable. Row values represent: position (cM), Predictive accuracy resistant phenotype, Predictive accuracy resistant phenotype, sample size and P-value.
SNP identifier

| PET_T313921\|C33345_11403 | PET_T34820\|C40921_6318 | PET_T32405\|C77170_70332 | PET_T318744\|C15244_14222 | PET_T34003\|C163871_61706 | PET_T34225\|C2660_1649 | PET_T32747\|C57711_6706 | PET_T310214\|C62940_5790 | PET_T36154\|C53573_29679 | PET_T38438\|C65290_10905 |
|---|---|---|---|---|---|---|---|---|---|
| 71.79 | 72.43 | 73.72 | 73.72 | 74.05 | 74.05 | 74.53 | 75.93 | 79.58 | 80.30 |
| 0.639 | 0.637 | 0.643 | 0.585 | 0.638 | 0.646 | 0.643 | 0.654 | 0.658 | 0.652 |
| 0.955 | 0.955 | 0.960 | 0.960 | 0.964 | 0.965 | 0.960 | 0.975 | 0.975 | 0.970 |
| 357 | 356 | 356 | 356 | 356 | 356 | 356 | 356 | 356 | 356 |
| 1.68E−36 | 2.48E−36 | 2.33E−37 | 1.71E−37 | 2.63E−38 | 3.64E−39 | 6.21E−38 | 2.84E−42 | 1.00E−42 | 6.68E−41 |

| | PET_T38438\|C65290_4524 | PET_T39109\|C61248_47335 | PET_T39109\|C61248_42383 | PET_T39109\|C61248_40929 | PET_T33755\|C82570_24205 | PET_T33755\|C82570_47754 | PET_T327258\|C21443_16338 | PET_T35302\|C48674_26268 | PET_T35205\|C39805_21235 |
|---|---|---|---|---|---|---|---|---|---|
| | 80.30 | 80.98 | 80.98 | 80.98 | 80.98 | 80.98 | 82.72 | 82.72 | 91.47 |
| | 0.642 | 0.642 | 0.642 | 0.642 | 0.619 | 0.642 | 0.631 | 0.631 | 0.615 |
| | 0.969 | 0.964 | 0.964 | 0.964 | 0.965 | 0.964 | 0.949 | 0.949 | 0.949 |
| | 355 | 356 | 356 | 356 | 356 | 356 | 355 | 355 | 356 |
| | 7.38E−40 | 9.84E−39 | 9.84E−39 | 9.84E−39 | 1.92E−38 | 9.84E−39 | 1.43E−34 | 1.43E−34 | 3.43E−33 |

CONCLUSIONS

Disclosed is a single genomic region explaining TMV resistance in *Petunia hybrida* which is different from WO 2007/097574;

Disclosed is a semi-dominant gene, as in conditions where temperatures were not controlled, ca 70% of plants in population 1 and 65.8% across both F1 populations with a single copy of the resistant allele are resistant (as measured by ELISA 2 WAI) and ca 95% of individuals homozygous for the recessive allele are susceptible (positive ELISA results 2 WAI).

Disclosed is that resistance is dependent on temperature and virus isolates. Individuals carrying a single copy of the resistant allele are more likely to develop a systemic infection when maintained at 31° C. (23%) than when they are maintained at 21° C. (17%).

The invention claimed is:

1. A plant selected from the group consisting of *Petunia alpicola, Petunia axillaris, Petunia bajeensis, Petunia bonjardinensis, Petunia exserta, Petunia guarapuavensis, Petunia inflata, Petunia integrifolia, Petunia interior, Petunia ledifolia, Petunia littoralis, Petunia mantiqueirensis, Petunia occidentalis, Petunia patagonica, Petunia reitzii, Petunia riograndensis, Petunia saxicola, Petunia scheideana, Petunia villadiana, Petunia violaceae* and hybrids thereof, wherein said plant is resistant to Tobamoviruses and comprises in its genome SEQ ID No. 1 and SEQ ID No. 3, and wherein said resistance is semi-dominant Tobamovirus resistance as found in deposit NCIMB 42982.

2. The plant according to claim 1, wherein said plant is *Petunia hybrida*.

3. The plant according to claim 1, wherein said plant was deposited under accession number NCIMB 42982.

4. The plant according to claim 1, wherein the resistance to Tobamovirus is selected from one or more of the group consisting of Tobacco mosaic virus resistance, Tomato mosaic virus resistance, Tobacco mild green mosaic virus resistance, and Pepper mild mottle virus resistance.

5. The plant according to claim 1, wherein the resistance to Tobamovirus is Tobacco mosaic virus resistance.

6. The plant according to claim 1, wherein said plant does not comprise in its genome SEQ ID No. 2 and/or SEQ ID No. 4.

7. The plant according to claim 1, wherein said plant is a *Petunia hybrida* and said Tobamovirus is Tobacco mosaic virus.

8. The plant according to claim 1, wherein said Tobamovirus resistance is encoded by a semi-dominant gene homozygously present in said plant.

9. A method for identifying a Tobamovirus resistant plant, comprising detecting the presence of SEQ ID No. 1 and SEQ ID No. 3 in the genome of said plant, wherein said plant is selected from the group consisting of *Petunia alpicola, Petunia axillaris, Petunia bajeensis, Petunia bonjardinensis, Petunia exserta, Petunia guarapuavensis, Petunia inflata, Petunia integrifolia, Petunia interior, Petunia ledifolia, Petunia littoralis, Petunia mantiqueirensis, Petunia occidentalis, Petunia patagonica, Petunia reitzii, Petunia riograndensis, Petunia saxicola, Petunia scheideana, Petunia villadiana, Petunia violaceae,* and hybrids thereof.

10. The method according to claim 9, wherein said method further comprises detecting the absence in the genome of said plant of SEQ ID No. 2 and/or SEQ ID No. 4.

11. The method according to claim 9, wherein said detecting comprises nucleic amplification and subsequent analysis of the amplification products.

12. The method according to claim 9, wherein the resistance to Tobamovirus to be identified is selected from one or more of the group consisting of Tobacco mosaic virus resistance, Tomato mosaic virus resistance, Tobacco mild green mosaic virus resistance, and Pepper mild mottle virus resistance.

13. The method according to claim 9, wherein said plant is *Petunia hybrida* and said Tobamovirus is Tobacco mosaic virus.

\* \* \* \* \*